United States Patent [19]
Bhatnagar et al.

[11] Patent Number: 5,661,127
[45] Date of Patent: Aug. 26, 1997

[54] PEPTIDE COMPOSITIONS WITH GROWTH FACTOR-LIKE ACTIVITY

[75] Inventors: Rajendra S. Bhatnagar, Burlingame; Jing Jing Qian, San Bruno, both of Calif.

[73] Assignee: The Regents of the University of California, Oakland, Calif.

[21] Appl. No.: 431,954

[22] Filed: May 1, 1995

[51] Int. Cl.$^6$ ............................. A61K 38/08; C07K 7/06
[52] U.S. Cl. ............................................. 514/16; 530/329
[58] Field of Search ............................... 514/16; 530/329

[56] References Cited

U.S. PATENT DOCUMENTS

| | | | |
|---|---|---|---|
| 5,002,583 | 3/1991 | Pitaru et al. | 623/66 |
| 5,055,447 | 10/1991 | Palladino et al. | 514/12 |
| 5,158,934 | 10/1992 | Ammann et al. | 514/12 |
| 5,171,574 | 12/1992 | Kuberasampath et al. | 424/423 |
| 5,178,845 | 1/1993 | Constantz et al. | 423/305 |
| 5,208,219 | 5/1993 | Ogawa et al. | 514/12 |
| 5,236,905 | 8/1993 | Brankovan et al. | 514/12 |
| 5,240,912 | 8/1993 | Todaro | 514/12 |
| 5,258,029 | 11/1993 | Chu et al. | 623/16 |
| 5,268,455 | 12/1993 | Cianciolo | 530/404 |
| 5,270,300 | 12/1993 | Hunziker | 514/12 |
| 5,284,763 | 2/1994 | Derynk et al. | 435/240.1 |
| 5,322,933 | 6/1994 | Davies et al. | 530/399 |
| 5,324,519 | 6/1994 | Dunn et al. | 424/426 |
| 5,364,839 | 11/1994 | Gerhart et al. | 514/12 |
| 5,368,858 | 11/1994 | Hunziker | 424/423 |

FOREIGN PATENT DOCUMENTS

| | | |
|---|---|---|
| 93/09228 | 5/1993 | WIPO . |
| 93/09229 | 5/1993 | WIPO . |

OTHER PUBLICATIONS

Archer et al., "Transforming Growth Factor β1: Secondary Structure as Determined by Heteronuclear Magnetic Resonance Spectroscopy," *Biochemistry*, 32, (1993), pp. 1164–1171.

Basler et al., "Control of Cell Pattern in the Neural Tube: Regulation of Cell Differentiation by dorsalin–1, a Novel TGFβ Family Member," *Cell*, 73, (May 21, 1993), pp. 687–702.

Berge et al., "Pharmaceutical Salts," *Journal of Pharmaceutical Sciences*, 66:1, (Jan. 1977), pp. 1–19.

Bone et al., "Definitions for Sepsis and Organ Failure and Guidelines for the Use of Innovative Therapies in Sepsis," *Chest*, 101:6 (Jun. 1992), pp. 1644–1655.

Daopin et al., "Crystal Structure of TGF–β2 Refined at 1.8 Å Resolution," *Proteins*, 17, (1993), pp. 176–192.

Hubbell and Langer, "Tissue Engineering," *Chemical and Engineering News*, (Mar. 13, 1995), pp. 42–54.

Massagué, "The Transforming Growth Factor–β Family," *Annu. Rev. Cell Biol.*, 6, (1990), pp. 597–641.

Termine and Posner, "Calcium Phosphate Formation in vitro: I. Factors Affecting Initial Phase Separation," *Archives of Biochemistry and Biophysics*, 140, (1970), pp. 307–317.

Termine et al., "Calcium Phosphate Formation in vitro: II. Effects of Environment of Amorphous–Crystalline Transformation," *Archives of Biochemistry and Biophysics*, 140, (1970), pp. 318–325.

Amatayakul–Chantler et al., "[Ser$^{77}$] Transforming Growth Factor–β1," *Journal of Biological Chemistry*, 269:44, (1994), pp. 27687–27691.

Chang et al., "Cartilage–derived Morphogenetic Proteins," *Journal of Biological Chemistry*, 269:45, (1994), pp. 28227–28234.

Chopra et al., "Newly Synthesized Proteoglycans Secreted by Sequentially Derived Populations of Cells from New–Born Rat Calvaria," *Cell Differentiation and Development*, 32, (1990), pp. 47–59.

Colletta et al., "The Growth Inhibition of Human Breast Cancer Cells by a Novel Synthetic Progestin Involves the induction fo Transforming Growth Factor Beta," *J. Clin. Invest.*, 87, (1991), pp. 277–283.

Galéra et al., "Effect of Transforming Growth Factor–β–1 (TGF–β1) on Matrix Synthesis by Monolayer Cultures of Rabbit Articular Chondrocytes during . . . ," *Experimental Cell Research*, 200 (1992), pp. 379–392.

Grande et al., "Transforming Growth Factor–β1 Induces Collagen IV Gene Expression in NIH–3T3 Cells," *Laboratory Investigation*, 69:4, (1993), pp. 387–395.

Günther et al., "Transforming Growth Factor β1 Regulates Tissue Inhibitor of Metalloproteinases–1 Expression in Differentiated Human Articular Chondrocytes," *Arthritis & Rheumatism*, 37:3, (1994), pp. 395–405.

Hamilton and Millis, "Developmental Roles for Growth Factor–Regulated Secreted Proteins," *Current Topics in Development Biology*, 24, (1990), pp. 193–218.

Li and Drucker, "Growth Facator–like Properties of Parathyroid Hormone–related Peptide in Transfected Rodent Cell Lines," *Cancer Research*, 53, (1993), pp. 2980–2986.

Lynch and Giannobile, "Polypeptide Growth Factors: Molecular Mediator of Tissue Repair," Chapter 33 in *Molecular Pathogenesis of Periodontal Disease*, (1994), pp. 415–425.

Massagué et al., "Multiple Type–β Transforming Growth Factors and Their Receptors," *Journal of Cellular Physiology Supplement*, 5, (1987), pp. 43–47.

(List continued on next page.)

*Primary Examiner*—Cecilia J. Tsang
*Assistant Examiner*—Anish Gupta
*Attorney, Agent, or Firm*—Majestic, Parsons, Siebert & Hsue

[57] ABSTRACT

A peptide has been synthesized with the sequence ANVAENA (SEQ ID NO:1). This peptide, designated "cytomodulin," is able to mimic a broad range of activities of TGF–β1 in various cell types. Compositions for applications such as tissue repair are provided that comprise a biocompatible matrix having cytomodulin admixed with or carried by the matrix.

9 Claims, 6 Drawing Sheets

OTHER PUBLICATIONS

Matrisian and Hogan, "Growth Factor–Regulated Proteases and Extracellular Matrix Remodeling during Mammalian Development," *Current Topics in Developmental Biology*, 24, (1990), pp. 219–259.

Nakanishi et al., "Expression of Nerve Growth Factor Family Neurotrophins in a Mouse Osteoblastic Cell Line," *Biochemical and Biophysical Research Communications*, 198:3, (1994), pp. 891–897.

Nogami et al., "Bioassay of Chondrocyte Differentiation by Bone Morphogenetic Protein," *Clinical Orthopaedics and Related Research*, 258, (1990), pp. 295–299.

O'Reilly et al., "Regulation of Expression of Transforming Growth Factor–$\beta 2$ by Transforming Growth Factor–$\beta$ Isoforms is Dependent upon Cell Type," *Growth Factors*, 6, (1992), pp. 193–201.

Rosen et al., "Bone Induction and Transforming Growth Factor–$\beta$," *Annals New York Academy of Sciences*, pp. 98–106 (1992).

Rutherford et al., "Induction of Reparative Dentine Formation in Monkeys by Recombinant Human Osteogenic Protein–1," *Archs oral Biol.*, 38:7, (1993), pp. 571–576.

Sampath et al., "Recombinant Human Osteogenic Protein–1 (hOP–1) Induces New Bone Formation in Vivo with a Specific Activity Comparable with . . . " *Journal of Biological Chemistry*, 267:28, (1992), pp. 20352–20362.

Saunders and D'Amore, "FGF and TFG–$\beta$: Actions and Interactions in Biolgoical Systems," *Critical Reviews in Eukaryotic Gene Expression*, 1:3, (1991), pp. 157–172.

Schwarz et al., "Aberrant TGF–$\beta$ Production and Regulation in Metastatic Malignancy," *Growth Factors*, 3, (1990), pp. 115–127.

Segarini, Patricia R., "Cell Type Specificity of TGF–$\beta$ Binding," *Annals New York Academy of Sciences*, pp. 73–89 (1990).

Sporn et al., "Some Recent Advances in the Chemistry and Biology of Transforming Growth Factor–Beta," *Journal of Cell Biology*, 105, (1987), pp. 1039–1045.

Taketazu et al., "Enhanced Expression of Transforming Growth Factor–$\beta$s and Transforming Growth Factor–$\beta$ Type II Receptors . . . ," *Laboratory Investigation*, 70:5, (1994), pp. 620–630.

van Beuningen et al., "Transforming Growth Facator–$\beta 1$ Stimulates Articular Chondrocyte Proteoglycan Synthesis and Induces Osteophyte Formation . . . ," *Laboratory Investigation*, 71:2, (1994), pp. 279–290.

Wozney et al., "Novel Regulators of Bone Formation: Molecular Clones and Activities," *Science*, 242, (1988), pp. 1528–1534.

Joyce et al., "Role of Transforming Growth Factor–$\beta$ in Fracture Repair," *Annals New York Academy of Sciences*, pp. 105–123 (1990).

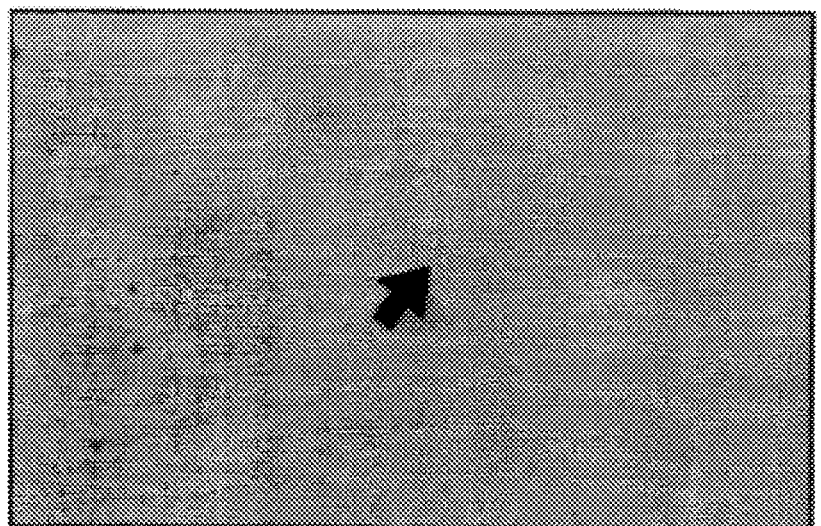
FIG._2A
CONTROL
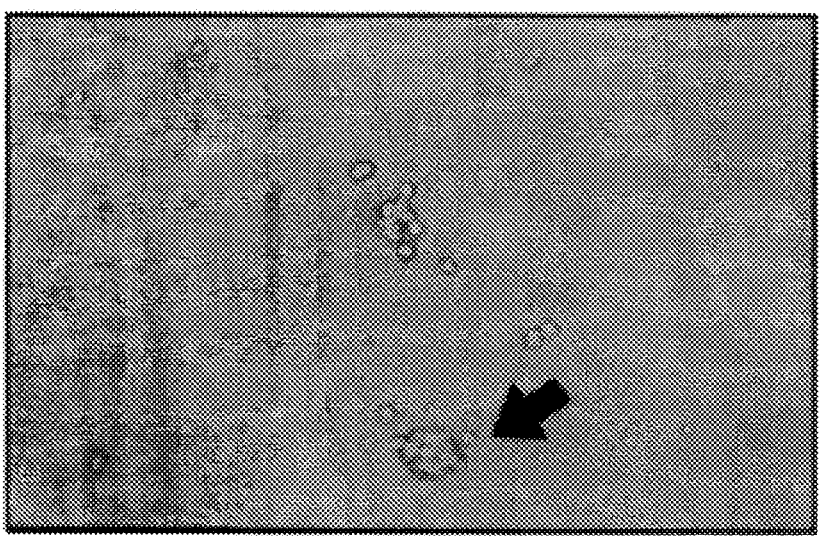
FIG._2B
FIG._2C

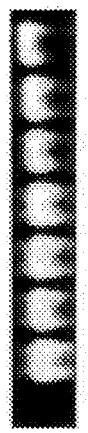 
CONTROL
CM  1nM
CM  10nM
CM  20nM
CM  50nM
CM  100nM
CM  200nM
FIG._4A
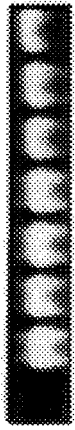 
CONTROL
CM  1nM
CM  10nM
CM  20nM
CM  50nM
CM  100nM
CM  200nM
FIG._4B
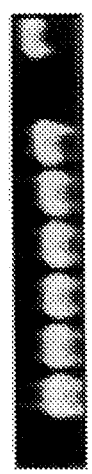 
CONTROL
CM  1nM
CM  10nM
CM  20nM
CM  50nM
CM  100nM
CM  200nM
FIG._4C
 
CONTROL
CM  1nM
CM  10nM
CM  20nM
CM  50nM
CM  100nM
CM  200nM
FIG._4D

FIG. 5(A)

| | | | | | | |
|---|---|---|---|---|---|---|
| 1 | H1 | ACE | 1 | 1.952 | 1.249 | .316 |
| 2 | CH3 | ACE | 1 | 1.927 | 2.333 | .203 |
| 3 | H2 | ACE | 1 | 1.576 | 2.782 | 1.133 |
| 4 | H3 | ACE | 1 | 1.243 | 2.593 | -.605 |
| 5 | C | ACE | 1 | 3.323 | 2.853 | -.119 |
| 6 | O | ACE | 1 | 4.272 | 2.077 | -.210 |
| 7 | N | ALA | 2 | 3.439 | 4.166 | -.310 |
| 8 | HN | ALA | 2 | 2.632 | 4.767 | -.211 |
| 9 | CA | ALA | 2 | 4.695 | 4.857 | -.543 |
| 10 | HA | ALA | 2 | 5.425 | 4.521 | .195 |
| 11 | CB | ALA | 2 | 5.211 | 4.572 | -1.957 |
| 12 | HB1 | ALA | 2 | 4.475 | 4.894 | -2.694 |
| 13 | HB2 | ALA | 2 | 6.142 | 5.115 | -2.122 |
| 14 | HB3 | ALA | 2 | 5.399 | 3.506 | -2.083 |
| 15 | C | ALA | 2 | 4.443 | 6.350 | -.361 |
| 16 | O | ALA | 2 | 3.292 | 6.788 | -.383 |
| 17 | N | ASN | 3 | 5.504 | 7.130 | -.187 |
| 18 | HN | ASN | 3 | 6.426 | 6.699 | -.147 |
| 19 | CA | ASN | 3 | 5.484 | 8.570 | .015 |
| 20 | HA | ASN | 3 | 4.836 | 9.029 | -.733 |
| 21 | CB | ASN | 3 | 4.964 | 8.871 | 1.432 |
| 22 | HB2 | ASN | 3 | 5.670 | 8.464 | 2.158 |
| 23 | HB3 | ASN | 3 | 4.000 | 8.383 | 1.578 |
| 24 | CG | ASN | 3 | 4.760 | 10.357 | 1.704 |
| 25 | OD1 | ASN | 3 | 4.723 | 11.177 | .792 |
| 26 | ND2 | ASN | 3 | 4.654 | 10.739 | 2.969 |
| 27 | HND1 | ASN | 3 | 4.656 | 10.052 | 3.709 |
| 28 | HND2 | ASN | 3 | 4.487 | 11.714 | 3.168 |
| 29 | C | ASN | 3 | 6.925 | 9.054 | -.180 |
| 30 | O | ASN | 3 | 7.816 | 8.242 | -.407 |
| 31 | N | VAL | 4 | 7.196 | 10.354 | -.082 |
| 32 | HN | VAL | 4 | 6.433 | 11.007 | .038 |
| 33 | CA | VAL | 4 | 8.563 | 10.863 | -.110 |
| 34 | HA | VAL | 4 | 9.001 | 10.579 | -1.068 |
| 35 | CB | VAL | 4 | 8.546 | 12.404 | -.038 |
| 36 | HB | VAL | 4 | 7.922 | 12.763 | -.857 |
| 37 | CG1 | VAL | 4 | 7.958 | 12.951 | 1.272 |
| 38 | HG11 | VAL | 4 | 8.590 | 12.684 | 2.119 |
| 39 | HG12 | VAL | 4 | 7.900 | 14.038 | 1.213 |
| 40 | HG13 | VAL | 4 | 6.955 | 12.563 | 1.438 |
| 41 | CG2 | VAL | 4 | 9.949 | 12.988 | -.245 |
| 42 | HG21 | VAL | 4 | 10.376 | 12.608 | -1.174 |
| 43 | HG22 | VAL | 4 | 9.889 | 14.075 | -.306 |
| 44 | HG23 | VAL | 4 | 10.605 | 12.718 | .583 |
| 45 | C | VAL | 4 | 9.414 | 10.217 | .994 |
| 46 | O | VAL | 4 | 10.604 | 9.986 | .807 |
| 47 | N | ALA | 5 | 8.808 | 9.966 | 2.157 |
| 48 | HN | ALA | 5 | 7.829 | 10.176 | 2.244 |
| 49 | CA | ALA | 5 | 9.520 | 9.482 | 3.331 |
| 50 | HA | ALA | 5 | 10.411 | 10.096 | 3.479 |

FIG. 5(B)

| | | | | | | |
|---|---|---|---|---|---|---|
| 51 | CB | ALA | 5 | 8.626 | 9.645 | 4.563 |
| 52 | HB1 | ALA | 5 | 7.723 | 9.042 | 4.457 |
| 53 | HB2 | ALA | 5 | 9.169 | 9.314 | 5.450 |
| 54 | HB3 | ALA | 5 | 8.350 | 10.693 | 4.688 |
| 55 | C | ALA | 5 | 9.968 | 8.025 | 3.185 |
| 56 | O | ALA | 5 | 11.076 | 7.684 | 3.587 |
| 57 | N | GLU | 6 | 9.079 | 7.168 | 2.682 |
| 58 | HN | GLU | 6 | 8.245 | 7.512 | 2.233 |
| 59 | CA | GLU | 6 | 9.204 | 5.720 | 2.725 |
| 60 | HA | GLU | 6 | 10.254 | 5.429 | 2.779 |
| 61 | CB | GLU | 6 | 8.456 | 5.210 | 3.964 |
| 62 | HB2 | GLU | 6 | 7.393 | 5.439 | 3.867 |
| 63 | HB3 | GLU | 6 | 8.837 | 5.712 | 4.854 |
| 64 | CG | GLU | 6 | 8.602 | 3.703 | 4.203 |
| 65 | HG2 | GLU | 6 | 9.655 | 3.443 | 4.313 |
| 66 | HG3 | GLU | 6 | 8.176 | 3.138 | 3.375 |
| 67 | CD | GLU | 6 | 7.861 | 3.290 | 5.467 |
| 68 | OE1 | GLU | 6 | 6.706 | 3.745 | 5.612 |
| 69 | OE2 | GLU | 6 | 8.468 | 2.548 | 6.266 |
| 70 | C | GLU | 6 | 8.583 | 5.188 | 1.438 |
| 71 | O | GLU | 6 | 7.633 | 5.781 | .930 |
| 72 | N | ASN | 7 | 9.123 | 4.107 | .882 |
| 73 | HN | ASN | 7 | 9.827 | 3.588 | 1.392 |
| 74 | CA | ASN | 7 | 8.673 | 3.542 | -.382 |
| 75 | HA | ASN | 7 | 7.595 | 3.676 | -.478 |
| 76 | CB | ASN | 7 | 9.390 | 4.236 | -1.545 |
| 77 | HB2 | ASN | 7 | 10.466 | 4.108 | -1.419 |
| 78 | HB3 | ASN | 7 | 9.155 | 5.301 | -1.530 |
| 79 | CG | ASN | 7 | 8.962 | 3.664 | -2.892 |
| 80 | OD1 | ASN | 7 | 7.842 | 3.197 | -3.055 |
| 81 | ND2 | ASN | 7 | 9.840 | 3.699 | -3.887 |
| 82 | HND1 | ASN | 7 | 10.757 | 4.091 | -3.746 |
| 83 | HND2 | ASN | 7 | 9.556 | 3.315 | -4.774 |
| 84 | C | ASN | 7 | 8.974 | 2.049 | -.371 |
| 85 | O | ASN | 7 | 9.950 | 1.634 | .253 |
| 86 | N | ALA | 8 | 8.148 | 1.245 | -1.035 |
| 87 | HN | ALA | 8 | 7.449 | 1.658 | -1.644 |
| 88 | CA | ALA | 8 | 8.215 | -.205 | -1.003 |
| 89 | HA | ALA | 8 | 9.244 | -.529 | -.837 |
| 90 | CB | ALA | 8 | 7.341 | -.717 | .150 |
| 91 | HB1 | ALA | 8 | 6.300 | -.440 | -.024 |
| 92 | HB2 | ALA | 8 | 7.415 | -1.800 | .241 |
| 93 | HB3 | ALA | 8 | 7.675 | -.269 | 1.087 |
| 94 | C | ALA | 8 | 7.762 | -.755 | -2.355 |
| 95 | O | ALA | 8 | 7.562 | -.002 | -3.304 |
| 96 | N | NME | 9 | 7.602 | -2.077 | -2.453 |
| 97 | HN | NME | 9 | 7.783 | -2.641 | -1.638 |
| 98 | CT | NME | 9 | 7.166 | -2.736 | -3.673 |
| 99 | HT1 | NME | 9 | 6.431 | -2.126 | -4.201 |
| 100 | HT2 | NME | 9 | 8.026 | -2.904 | -4.322 |
| 101 | HT3 | NME | 9 | 6.712 | -3.695 | -3.424 |

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
(A) LENGTH: 7 amino acids
(B) TYPE: amino acid
(D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:1:

```
Ala  Asn  Val  Ala  Glu  Asn  Ala
1                    5
```

PEPTIDE COMPOSITIONS WITH GROWTH FACTOR-LIKE ACTIVITY

FIELD OF THE INVENTION

The invention generally relates to growth factors and neurotrophic factors, and more particularly to a small, synthetic peptide having (or mimicking) TGF-β growth factor activity and to matrices and compositions including the small peptide.

BACKGROUND OF THE INVENTION

Growth factors are substances, such as poly-peptide hormones, which affect the growth of defined populations of animal cells in vivo or in vitro, but which are not nutrient substances. Proteins involved in the growth and differentiation of tissues may promote or inhibit growth, and promote or inhibit differentiation, and thus the general term "growth factor" includes cytokines and trophic factors.

Growth factors typically are polypeptides ranging in molecular weights from 5000 to 50,000 daltons. Based on structural similarities, growth factors are categorized into families which include: insulin-like growth factors (IGFs), platelet-derived growth factors (PDGFs), fibroblast growth factors (FGFs), epidermal growth factors (EGFs), nerve growth factors (NGFs), and transforming growth factors type-beta (TGF-βs).

Transforming growth factor-βs were originally named for their ability to transform normal fibroblasts to cells capable of anchorage-independent growth. However, despite the name, TGF-βs are multifunctional growth factors that are required for the normal development, growth, and differentiation of various epithelial, endothelial, and mesenchymal cells. As with other cytokines, the specific effect of TGF-βs depend on the particular cell type and its surrounding environment.

The effects of TGF-βs on cells are generally classified as proliferative and non-proliferative. As originally established with the first experiments on fibroblasts, TGF-βs are bona fide growth factors. Two important cell types in which proliferation is enhanced by TGF-β are osteoblasts and Schwann cells of the peripheral nervous system. However, in many cells, TGF-βs are potent inhibitors of cell proliferation. This negative growth control may be the regulatory mechanism that checks regeneration of certain tissues and may play a role in the initiation of carcinogenesis.

The most important non-proliferative function of TGF-βs are in enhancing the formation of extracellular matrices. Although this is achieved primarily through the increased transcription of both collagen and fibronectin, the inhibition of the proteases from degrading the matrix also contributes to its stability. Degradation of the extracellular matrix is inhibited by the decrease in the secretion of the proteases themselves and the simultaneous increase in the levels of protease inhibitors. The marked and generalized effect of TGF-β on extracellular matrices is likely to play a major role in tissue repair processes and the pathogenesis of certain fibrotic diseases.

DNA encoding several different receptors for TGF-β has recently been described by Lin et al., PCT application WO93/09228, published May 13, 1993. The availability of the TGF-β receptors will facilitate further assessments of TGF-β functions.

Many members of the TGF-β super family have been characterized. For example, Basler et al. have graphically represented the sequence relationship between members of the TGF-β superfamily. *Cell*, 73, pp. 687–702 (1993). Massagué, *Annu. Rev. Cell Biol.*, 6, pp. 597–641 (1990) also reviews the transforming growth factor-β family, including a discussion of the mechanisms of TGF-β actions. An NMR characterization of the secondary structure of TGF-β1 has been reported, and a refined 3-dimensional crystal structure of TGF-β2 described, by Daopin et al., *Proteins*, 17, pp. 176–192 (1993). The monomer of TGF-β2 adopts a fold that resembles a slightly curled left hand with two anti-parallel β-sheets forming four fingers of the hand. These four finger regions together with conserved disulfides define the fold for the TGF-β superfamily.

Also among TGF-β members are the bone morphogenetic proteins (BMP). The BMPs have been indicated as useful in wound healing, tissue repair, and to induce cartilage and/or bone growth. For example, PCT Application 9309229, inventors Israel and Wolfman, published May 13, 1993, describes uses of proteins with bone stimulating activity such as bone fracture healing and possibly the treatment of periodontal disease and other tooth repair processes. A recent special article by *C&EN*, Hubbell and Langer, pp. 42–54 (Mar. 13, 1995) reports that a BMP has been incorporated into polymer particles so that as the polymer degrades, the protein is slowly released to surrounding tissues, where it stimulates the migration of cells into the porous matrix and, ultimately, the synthesis of new bone. The article also notes that bone has been produced by slowly releasing TGF-β.

Because of the wide applicability of TGF-βs in clinical therapies, they have been the focus of much research. Although much of the research involved in vitro uses, recent in vivo studies have confirmed some of the more promising in vitro effects. As a consequence, some of the possible clinical uses for TGF-βs include the stimulation of angiogenesis, the formation of granulation tissue associated with wound healing, and the formation of bone and cartilage.

Nucleic acid encoding TGF-β and a variety of uses for TGF-β are described in U.S. Pat. No. 5,284,763, issued Feb. 8, 1994, inventors Derynk and Goeddel. U.S. Pat. No. 5,258,029, issued Nov. 2, 1993, inventors Chu et al. describe preparations of stress-bearing prothesis with bony ingrowth occurring after implantation, which prothesis includes TGF-β carried by a collagen composition or a ceramic. U.S. Pat. No. 5,368,858, issued Nov. 29, 1994, inventor Hunziker describes preparations of biodegradable matrices including TGF-βs as proliferation agents, chemotactic agents, and transforming factors.

U.S. Pat. No. 5,055,447, inventors Palladino et al., issued Oct. 8, 1991, describes methods and compositions for the treatment or prophylaxis of Septic shock caused by bacteremic infection. Thus, for example, this patent teaches a therapeutic method for a patient suffering from or at risk of septic shock by administering transforming growth factor-β. Recently, the concept of "sepsis" has been viewed more broadly as an inflammatory condition, and a group of researchers have suggested the designation "systemic inflammatory response syndrome" to describe both "sepsis" (infection by the presence of bacteria in the blood stream) as well as other (non-septic) inflammatory conditions. *Chest*, 101, pp. 1644–1655 (1992).

Thus, growth factors are useful in a number of therapeutic, clinical, research, diagnostic, and drug design applications. However, as previously mentioned, growth factors are typically large. The natural members of the transforming growth factor-β family range upwards of 25

KDa molecular weight. Clinical uses of growth factors, including TGF-βs, may be limited because of their size, such as due to causing immune responses. For example, human TGF-β1 is a 25,000 dalton homodimeric protein. In addition to possible adverse immunological responses, large proteins are not often the best candidates for drugs because of the difficulties in administration and delivery.

Consequently, small peptide mimics of natural growth factors which would avoid most of these problems would be desirable for applications including those to which TGF-β has been put or suggested. It would be advantageous to have small peptides mimicking the biological activity of the large, natural members since small peptides on a mole per mole basis would require much smaller net amounts for administration, and topical applications would be more feasible. Also, quite small peptides would tend to have little or no adverse immunological responses, and could be synthesized easily using simple peptide chemistry procedures.

SUMMARY OF THE INVENTION

The present invention describes the characterization, properties, and uses of a novel peptide, which is called "cytomodulin." Cytomodulin is able to mimic the broad range of activities of TGF-β1 in various cell types. Moreover, initial results with human osteogenic sarcoma (HOS) cell line indicate that cytomodulin also may be a mimic for other members of the TGF-β superfamily, such as bone morphogenic proteins (BMPs) and osteogenic protein (OPs), as evidenced by its ability to specifically stimulate markers (alkaline phosphatase and osteonectin) characteristic of the osteoblast phenotype.

This novel compound we call "cytomodulin" has the amino acid sequence: Ala-Asn-Val-Ala-Glu-Asn-Ala (SEQ ID NO:1) and is readily synthesized by techniques known to the art. Thus, in one aspect of the present invention a biologically active peptide is provided having the amino acid sequence set forth in SEQ ID NO:1.

In another aspect of the present invention, a composition for tissue repair comprises a biocompatible matrix combined with a peptide (growth factor) having substantially the same SEQ ID NO:1 amino acid sequence. The biocompatible matrix may be biodegradable or nonbiodegradable. The peptide is admixed with or carried on the matrix in an amount effective to promote cell growth. Such matrices are useful in constructing templates for repair of soft and hard tissues, for rapid replacement of lost tissue, and for reconstructive and plastic surgery. Such composites provide and sustain cellular regeneration, and can be used in combination with other growth factors although surprisingly a preferred peptide embodiment of the invention induces fibroblast colony formation without the presence of additional growth factors such as epidermal growth factor and platelet-derived growth factor.

In yet another aspect of the present invention, a pharmaceutical formulation is provided comprising substantially the same SEQ ID NO:1 compound (which may be in salt form), and a physiologically compatible carrier.

The SEQ ID NO:1 compound that we have termed "cytomodulin" has biological activity that mimics at least one biological activity of TGF-βs, such as inhibiting DNA synthesis in Mv-1-Lu mink lung epithelial cells, promoting growth and colony formation by NRK-49 F fibroblasts, inducing increased expression of type I collagen, and/or inducing TGF-β expression.

BRIEF DESCRIPTION OF THE DRAWINGS

FIG. 2 are photomicrographs (magnification 500 times) wherein FIG. (A) is a control, FIG. (B) is with 100 nM cytomodulin, and FIG. (C) is 100 nM cytomodulin plus EGF and PDGF, all five days in soft agar with NRK-49 F normal rat kidney fibroblasts;

FIG. 4 having panels (A) through (D) are Northern Blots corresponding to the data graphically illustrated by FIG. 3 and its respective FIGS. (A)-(D); and FIG. 5 gives the atomic coordinates for atom numbers 1–101 of the cytomodulin embodiment of the invention.

DESCRIPTION OF THE PREFERRED EMBODIMENTS

Figure 1:
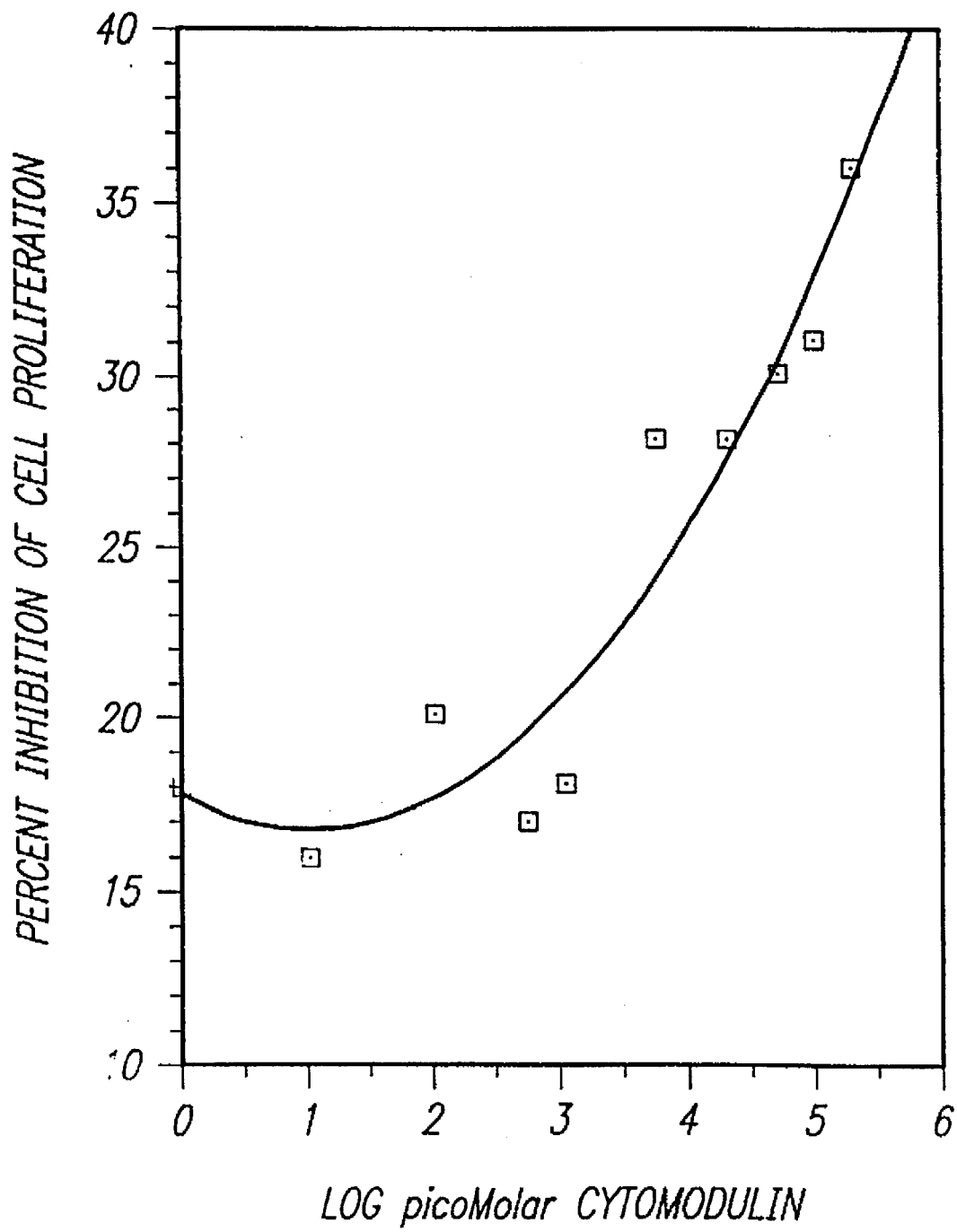
FIG. 1 graphically illustrates the inhibition of DNA synthesis of Mv-1-Lu mink lung epithelial cells by cytomodulin.
Figure 3B:
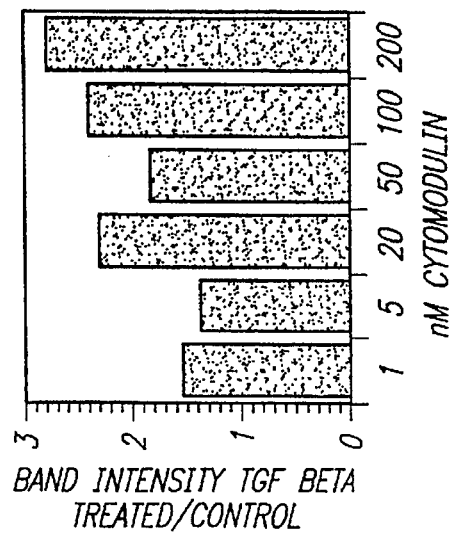
FIG. 3 graphically illustrates the modulation of gene expression in HOS cells by cytomodulin, where FIGS. (A), (B), and (D) show increased expression while FIG. (C) modulated activity depending on concenration, which is however quite characteristic of TGF-β in cells.
Figure 3D:
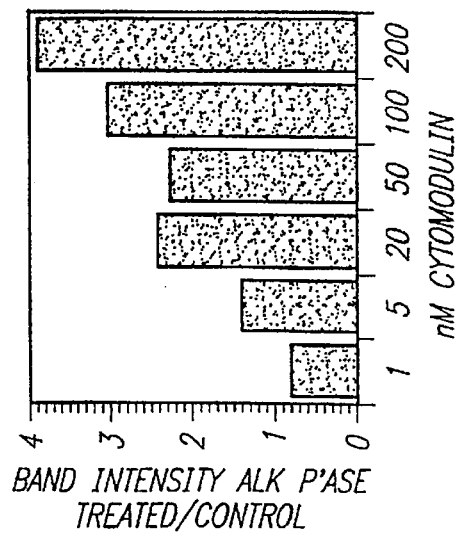
Figure 3A:
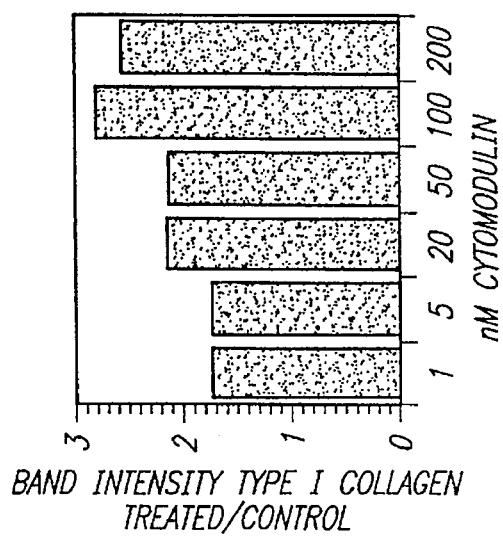
Figure 3C:
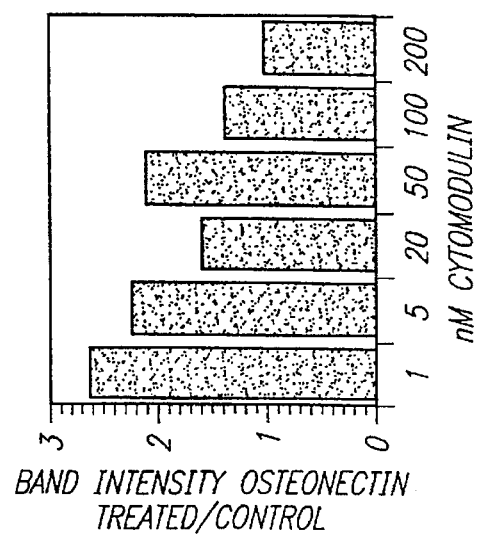

Peptides of this invention have a stable β-bend formed by -Val-Ala- at physiologic conditions. This stable β-bend is stabilized by at least one proximate charged amino acid residue. We have termed the novel compound "cytomodulin." This novel compound we call "cytomodulin" has the amino acid sequence: Ala-Asn-Val-Ala-Glu-Asn-Ala (SEQ ID NO:1) and is readily synthesized by procedures well known to the art.

The peptide can be synthesized by various suitable methods, preferably by solid phase synthesis, manual or automated, as first developed by R. B. Merrifield and described by J. M. Stewart and J. D. Young in "Solid Phase Peptide Synthesis" (1984). Chemical synthesis joins the amino acids in the predetermined sequence starting at the C-terminus. Basic solid phase methods require coupling the C-terminal protected α-amino acid to a suitable insoluble resin support. Amino acids for synthesis require protection on the α-amino group to ensure proper peptide bond formation with the preceding residue (or resin support). Following completion of the condensation reaction at the carboxyl end, the α-amino protecting group is removed to allow the addition of the next residue. Several classes of α-protecting groups have been described, see J. M. Stewart and J. D. Young in "Solid Phase Peptide Synthesis" (1984), with the acid labile, urethan-based tertiary-butyloxycarbonyl (Boc) being the historically preferred. Other protecting groups, and the related chemical strategies, may be used, including the base labile 9-fluorenylmethyloxycarbonyl (FMOC). Also, the reactive amino acid sidechain functional groups require blocking until the synthesis is completed. The complex array of functional blocking groups, along with strategies and limitations to their use, have been reviewed by M. Bodansky in "Peptide Synthesis" (1976) and, J. M. Stewart and J. D. Young in "Solid Phase Peptide Synthesis" (1984).

Solid phase synthesis is initiated by the coupling of the described C-terminal α-protected amino acid residue. Coupling requires activating agents, such as dicyclohexycarbodiimide (DCC) with or without 1-hydroxybenzo-triazole (HOBT), diisopropylcarbodiimide (DIIPC), or ethyldimethylaminopropylcarbodiimide (EDC). After coupling the C-terminal residue, the α-amino protected group is removed by trifluoroacetic acid (25% or greater) in dichloromethane in the case of acid labile tertiary-butyloxycarbonyl (Boc) groups. A neutralizing step with triethylamine (10%) in dichloromethane recovers the free amine (versus the salt). After the C-terminal residue is added to the resin, the cycle of deprotection, neutralization and coupling, with intermediate wash steps, is repeated in order to extend the protected peptide chain. Each protected amino acid is introduced in excess (three to five fold) with equimolar amounts of coupling reagent in suitable solvent. Finally, after the completely blocked peptide is assembled on the resin support, reagents are applied to cleave the peptide form the resin and to remove the side chain blocking groups. Anhydrous hydrogen fluoride (HF) cleaves the acid labile tertiary-butyloxycarbonyl (Boc) chemistry groups. Several nucleophilic scavengers, such as dimethylsulfide and anisole, are included to avoid side reactions especially on side chain functional groups.

We have prepared cytomodulin which, when added to cells in culture in the concentration range $10^{-9}$ to $10^{-6}$M (1.4 pg/mil to 1400 pg/mil), elicits certain highly specific effects in several different cell types, and thus evidences growth factor mimetic behavior. For example, among the effects observed is the inhibition of DNA synthesis in Mv-1-Lu mink lung epithelial cells, the growth and colony formation by NRK-49 F fibroblasts in soft agar, the induction of increased expression of type I collagen both in primary cultures of neo-natal human dermal fibroblasts as well as in HOS (human osteogenic sarcoma) cell line, and the induction of transforming growth factor $\beta$ expression.

The novel Val-Ala $\beta$-bend peptide is believed to find uses as agents for enhancing the survival or inducing the growth of nerve and muscle cells. Cytomodulin is, of course, useful as a new component of culture media for use in culturing nerve cells in vitro. This peptide also has utility as a substitute for the natural cytokines in many fields including: in surgery as agents which promote wound healing and regeneration; in orthopedics in promoting bone repair and implant integration; in dentistry in the repair of bony defects and in implant integration; in cancer chemotherapy and in radiation treatment as cytostatic agents for protection of normal stem cells against cell-cycle specific procedures; in treatment of rheumatoid arthritis; in ophthalmology for the repair of macular injury; in ophthalmology for the treatment of uveitis; as a protective agent for splanchnic artery occlusion reperfusion injury; and, as reagents for research in the biology of growth factors.

Therapeutic compositions of this invention will include the novel Val-Ala $\beta$-bend peptide in concentrations that depend upon the effective doses required and the modes of administration used. Various therapeutic indications for cytomodulin compositions will readily come to mind. One first indication is topical application to incisions or exposed tissue for the promotion of wound healing. The types of wound or other traumata that can be treated include (but are not limited to): first, second, and third degree burns (especially second and third degree); epidermal and internal surgical incisions, including those of cosmetic surgery; wounds, including lacerations, incision, and penetrations; and epidermal ulcers including decubital (bed-sores), diabetic, dental, hemophiliac, and varicose.

Uses may be by a variety of ways, such as systemic administration, topical application, intravenous administration, subcutaneous administration, intra-peritoneal injection, sub-periosteal injection, intra-tracheal administration, release from polymers or pumps, implants, or release from liposomes. Suitable implants (if using an implanted device) include, for example, gel foam, wax, or microparticle-based implants. Doses used should be sufficient to achieve circulating plasma concentrations of active ingredient that are efficacious. Effective doses may be extrapolated from dose-response curves derived from in vitro or animal model test systems.

The novel cytomodulin also is useful for inducing growth of bone. Thus, osteogenically effective amounts of the novel peptide in a pharmaceutically acceptable carrier or excipient can be administered for inducing deposition and maturation of bone at the site. In addition, the cytomodulin can be admixed with or carried by biomaterials, such as hydroxyapatite for bone generation or repair applications in a method such as is described by U.S. Pat. No. 5,158,934, issued Oct. 27, 1992, U.S. Pat. No. 5,208,219, issued May 4, 1993, by compositions such as described in U.S. Pat. No. 5,178,845, issued Jan. 12, 1993, all incorporated herein by reference.

Such bone repair compositions typically include various calcium phosphate mineral component materials such as, for example, hydroxyapatites commercially available under the designations Synthograft, Tricalcium Phosphate, or Periogras. The hydroxyapatite (or tricalcium phosphate) may be prepared by known methods rather than commercially purchased, such as those disclosed by Termine et al., *Arch. Biochem. Biophys.*, 140, TP307–325 (1970). Such a material can be supplied as a powder with preferred particle sizes typically in the range of about 100–2,000μ.

Another therapeutic indication for cytomodulin compositions of the invention is in conjunction with matrix forming materials. Preferably, the formulations include a matrix that is capable of providing a structure for developing bone and cartilage. Potential matrices may be biodegradable or nonbiodegradable, and may be chemically or biologicall defined.

For one example, the matrix can be inert, solid and non-porous, such as known and presently used as vessels for cell culture.

Another form that may be taken by matrices of this invention is that of soluble polymers.

Other suitable matrices for practice of this invention include various polymers and hydrogels. Such composites are useful in constructing templates for repair of soft tissue, for rapid replacement of lost tissue, and for reconstructive and plastic surgery.

Composites of the invention can thus be made with resorbable polymers of various kinds, having peptide carried by or grafted onto the lattice of the polymeric material. Of course, polymeric supports that are limited in resorbable properties such as hydroxyethyl methacrylate, polymethylmethacrylate, and N-vinylpyrrolidone methylmethacrylate, as a few examples, are also feasible. The composites can then be implanted in the tissue defect.

Among the known and suitable resorbable hydrogels are combinations of polylactacte and poly-glycollate. Compounds of the invention can be covalently bound to such materials during synthesis of the polymers themselves or the polymers can be hydrolyzed such that attachment sites are available by irradiating the polymer or by chemically activating the polymer to generate free radicals. Then conventional techniques for grafting, or immobilizing, peptides onto polymer supports can be utilized to prepare inventive composites. Resorbable hydrogels or polymers so prepared are particularly useful for soft tissue reconstructions. For hard tissue reconstructions or repair (e.g., bone repair) it is desirable to combine such water soluble, or resorbable, polymer species with a bioceramic, such as for example bioglass, aluminum oxide, calcium aluminate, tricalcium phosphate, and hydroxyapatite.

When cytomodulin is prepared for administration by mixing with physiologically acceptable carriers, i.e., carriers which are non-toxin to recipients at the dosages and concentrations employed, this will normally entail combining cytomodulin with buffers, antioxidants such as ascorbic acid, low molecular weight (less than about 10 residues) polypeptides, proteins, amino acids, carbohydrates including glucose or dextrins, chelating agents such as EDTA, and other excipients. Cytomodulin for use in therapeutic administrations must be sterile. This is readily accomplished by filtration through sterile filtration (0.22 micron) membranes.

The novel Val-Ala β-bend peptide may be administered in any pharmacologically acceptable carrier, and depending upon the desired mode of administration, may be formulated along with liquid carrier into liposomes, microcapsules, polymers or wax-based and controlled release preparations, or be formulated into tablet, pill, or capsule forms.

The peptide forms pharmaceutically acceptable salts with organic and inorganic acids and can be administered in salt form or the novel peptide can be amidated. Examples of suitable acids for the formation of pharmaceutically acceptable salts are hydrochloric, sulfuric, phosphoric, acetic, benzoic, citric, malonic, salicylic, malic, fumaric, succinic, tartaric, lactic, gluconic, ascorbic, maleic, benzene-sulfonic, methane- and ethanesulfonic, hydroxymethane- and hydroxyethane-sulfonic.

Salts may also be formed with suitable organic pharmaceutically acceptable base addition salts. These organic bases form a class whose limits are readily understood by those skilled in the art. Merely for purposes of illustration, the class may be said to include mono-, di-, and trialkylamines, such as methylamine, dimethylamine, and triethylamine; mono-, di-, or trihydroxyalkylamines such as mono-, di-, and triethanolamine; amino acids such as arginine, and lysine; guanidine; N-methyl-glucosamine; N-methylglucamine; L-glutamine; N-methylpiperazine; morpholine; ethylenediamine; N-benzylphenethylamine; tris(hydroxymethyl)aminomethane; and the like. (See, for example, "Pharmaceutical Salts," *J. Pharm. Sci.*, 66(1), 1–19 (1977).)

Therapeutic formulations of cytomodulin, such as for promoting bone cell growth, may be prepared for storage by mixing the novel peptide having the desired degree of purity with optional physiologically acceptable carriers, excipients or stabilizers, in the form of lyophilized cake or aqueous solutions. Acceptable carriers, excipients or stabilizers are nontoxic to recipients at the dosages and concentrations employed when administered, and include buffers such as phosphate, citrate, and other organic acids; anti-oxidants including ascorbic acid; low molecular weight (less than about 10 residues) polypeptides; proteins, such as serum albumin, gelatin or immunoglobulins.

Other components can include glycine, blutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN, PLURONICS or PEG. Yet additional useful components desirably included in therapeutic formulations of cytomodulin are one or more other growth factors, such as, for example, epidermal growth factor (EGF) and platelet-derived growth factor (PDGF).

Initial dosing of cytomodulin for topical applications such as wound healing should be delivered to the therapeutic site in a concentration of about from 50 to 500 ng/ml and thereafter adjusted in line with clinical experience. Since cytomodulin compositions both provide and sustain cellular regeneration, a continual application or periodic reapplication of the compositions is indicated. The clinician will be expected to modify the dosage in accordance with clinical experience.

Cytomodulin compositions may be used in the form of a sterile irrigant, preferably in combination with a physiological saline solution, or in the form of ointments or suspensions, preferably in combination with other growth factors as earlier noted, and yet further with collagen, a collagen analogue, or a collagen mimic, such as is described, for example, U.S. Pat. No. 5,354,736, issued Oct. 11, 1994, inventor Bhatnagar, incorporated herein by reference. The compositions also may be impregnated into transdermal patches, plasters, and bandages, preferably in a liquid or semi-liquid form. Automicrobial agents such as silver sulfadiazine should be included in such articles or compositions.

Cytomodulin also may be administered systemically for the treatment of wounds and similar traumata. Systemic administration is useful provided that there are no, or limited, undesirable side-effects, such as the stimulation of neoplastic cellular growth in patients with cancer. Cytomodulin compositions for systemic administration preferably are formulated as sterile, isotonic parenteral injections or infusions.

Cytomodulin compositions, as earlier described, either with cytomodulin alone or in combination with other growth factors, collagen, physiologically acceptable carriers, excipients, or stabilizers as described, may be carried by (or admixed with) a biologically compatible matrix. Matrices of the invention can be porous, and in bead, particulate, or fibrous forms. For example, calcium phosphate materials, such as apatite-based ceramics, have been suggested for producing porous tissue implants or prosthesis materials with micropores sufficient to permit tissue attachment. Thus, a therapeutic application for cytomodulin compositions of the invention is where the matrix forming material is biodegradable and can be used, for example, in cartilage repair.

Matrix materials useful for filing or otherwise dressing a defect in the cartilage include, for example, fibrinogen (activated with thrombin to form fibrin in the defect or lesion), collagen, gelatin or any other biodegradable material which forms a matrix with pores sufficiently large to allow repair cells to populate and proliferate within the matrix and which can be degraded and replaced with cartilage during the repair process.

The matrices useful in the compositions and methods of this invention may be preformed or may be formed in situ, for example, by polymerizing compounds and compositions such as fibrinogen to form a fibrin matrix. Matrices that may be preformed can include collagen, collagen analogues or collagen mimics (e.g., collagen sponges and collagen fleece), chemically modified collagen, gelatin beads or sponges, gel-forming substances, any other gel forming or composite substance that is composed of a biodegradable matrix material that will fill the tissue or bone defect and allow repair cells to populate the matrix, or mixtures of the above.

Biological activities of cytomodulin will now be further illustrated by the following examples, which are intended to be illustrative and not limiting.

EXAMPLE 1

Inhibition of DNA Synthesis of Mv-1-Lu Mink Lung Epithelial Cells

The effect of TGF-β and cytomodulin were evaluated by determining the rate of [$^1$H]thyidine incorporation into total acid-insoluble DNA and cell number. See generally, Sampath et al., *Journal of Biological Chemistry*, 267, pp. 20352–20362 (1992). DNA synthesis rates were determined in triplicate cultures after 24 hour treatment with various concentrations ($10^{-9}$M to $10^{-6}$M) of either TGF-$\beta$ or cytomodulin (which was synthesized by the Merrifield method) by adding [methyl-$^3$H]thymidine (2 µCi/ml, 80 Ci/mmol) for 6 hours before the termination of the culture. Incorporation was terminated by aspiration of the medium, and after washing three times with phosphate-buffered saline, the trichloroacetic acid (10%)-precipitated radioactive DNA was extracted with 1.0% (w/v) sodium dodecyl sulfate, 0.1M NaOH and quantitated by liquid scintillation counting. For cell number determination, $1 \times 10^5$ cells were plated in flasks in MEM containing 10% FBS, and after 24 hours, the growth medium was replaced with serum-free medium containing various conceptions of TGF-$\beta$ and cytomodulin. Triplicate cultures were harvested every 24 hours for the duration of 7 days, and the cell number was determined by counting cells released by trypsin digestion in a fixed volume hemacytometer.

The growth inhibition curve for cytomodulin were similar to that observed for TGF-$\beta$ at the same concentration range.

EXAMPLE 2

Growth and Colony Formation by NRK-49 F Fibroblasts in Soft Agar.

The original assay for TGF-$\beta$, the ability to promote anchorage independent growth of normal fibroblasts is still one of the hallmarks of TGF-$\beta$ activity. NRK-49 F fibroblasts were grown at 37° C. in DEM supplemented with 10% fetal calf serum. The experiments were performed with culture medium, 10 ng/mg epidermal growth factor (EGF), and 10 ng/ml platelet-derived growth factor (PDGF); however, unlike TGF-$\beta$, which does not induce colony formation in the absence of these factors (see, for example, Massagu, *J. Biol. Chem.*, 259, pp. 9756–9761 (1984)), cytomodulin did induce colony formation without these two growth factors. To this, either 100 nM TGF-β (positive control) or 100 nM cytomodulin was added. NRK-49 F fibroblasts ($5\times10^4$ cells/ml) were mixed with 0.3% agar were plated on the bottom of 35 mm culture dishes. Colony formation was observed starting on day 3 of culture.

As expected no colonies were formed in those cultures containing only the basic medium. Also, as expected, colonies with TGF-β grew colonies. Surprisingly, the cytomodulin cultures also formed colonies to approximately the same extent as the TGF-β cultures. The growth characteristics of the colonies over time were similar between TGF-β and cytomodulin cultures.

With reference to FIG. 2, photomicrographs are illustrated that were taken on day 5 of the fibroblast culturing. Colony formation was actually observed starting on day 3 of culture. As seen in FIG. 2(A), few cells survived culture in the absence of any growth factors. FIG. 2, Panel (B) and Panel (C) show the formation of small colonies (arrows) in the presence of cytomodulin, with Panel (C) also including EGF and PDGF, which induced much larger colonies (arrows). This is analogous to the induction of colony formation by TGF-β, except that TGF-β requires the concomitant presence of epidermal growth factor (EGF) and platelet derived growth factor (PDGF); however, as seen by Panel (B), cytomodulin did induce colony formation by itself.

EXAMPLE 3

RNA Isolation and Northern Analysis

Total cellular RNA was isolated using essentially the method described by Maniatis. Sambrook et al., *Molecular Cloning: A Laboratory Manual*, Cold Spring Harbor Laboratory Press, Second Edition (1989). Cells were lysed with 0.5% SDS and 0.1 potassium acetate. The lysate was extracted with phenol and centrifuged at 5000 rpm for 15 minutes. The aqueous phase was precipitated with 2 volumes ethanol in 0.1M Tris, pH 8.0 and 0.2M NaCl. The pellet was resuspended and quantitated by measuring the ultraviolet absorbance at 260 nm. RNA purity was assessed by comparing the ultraviolet absorbance at 260 nm with that at 280 nm.

RNA (10 μg/lane) was electrophoresed at 3 to 4 v/cm through a 0.7% agarose, 2.2M formaldehyde denaturing gel. RNA was transferred by capillary transfer to nylon membranes. RNA integrity, gel loading, and transfer efficiency were assessed by methylene blue stained 28 S and 18 S bands. The filters were baked at 80° C. for 2 hours to immobilize the RNA. After baking, the filters were hybridized at 65° C. in 0.5M $NaPO_4$ buffer, pH 7.0, containing 1 mM EDTA, 7% sodium dodecyl sulfate, and 1% bovine serum albumin. cDNA probes were labeled with dDIG (fluorescent probe) by the random primer method, using Klenow enzyme. Hybridization for 18 hours at 65° C. followed by washing, was performed.

Data were analyzed by scanning digoxigenin-dVTP according to manufacturer's procedure (Boehringer Mannheim Biochemica, DIG DNA labelling kit, Cat. No. 1175033).

Turning to FIG. 5, the atomic coordinates of the bioactive structure of cytomodulin are given (atoms 1–101). Thus, FIG. 5 describes the biologically active surface of the inventive peptide. We believe analogues may be synthesized presenting the same or substantially the same surface to cell membrane receptors so as to be equivalent to the inventive cytomodulin. Alternatively, compounds may be synthesized within increased or decreased activity with respect to cytomodulin by exploiting allosteric binding mechanisms. Thus, embodiments of the invention, such as compositions useful for tissue repair, comprise a biocompatible matrix and a peptide having substantially the amino acid sequence of cytomodulin in that cytomodulin itself or analogues thereof, when admixed with or carried on the matrix and present in an amount effective to promote cell growth, will present the same or substantially the same biologically active surface as is illustrated by FIG. 5.

It is to be understood that while the invention has been described above in conjunction with preferred specific embodiments, the description and examples are intended to illustrate and not limit the scope of the invention, which is defined by the scope of the appended claims.

We claim:

1. A biologically active peptide having the amino acid sequence Ala-Asn-Val-Ala-Glu-Asn-Ala (SEQ ID NO:1).

2. A composition useful for tissue repair, comprising:
a biocompatible matrix; and
a peptide having the amino aid sequence Ala-Asn-Val-Ala-Glu-Asn-Ala (SEQ ID NO:1) admixed with or carried on the matrix and in an amount effective to promote cell growth.

3. The composition as in claim 2 wherein the amino acid sequence has a -Val-Ala-, which forms a stable β-bend at physiologic conditions.

4. The composition as in claim 2 wherein the biocompatible matrix is biodegradable.

5. The composition as in claim 4 wherein the matrix includes a resorbable polymer.

6. The composition as in claim 2 wherein the biocompatible matrix is non-biodegradable.

7. The composition as in claim 6 wherein the matrix is porous.

8. A pharmaceutical formulation, comprising:

a compound having the amino acid sequence Ala-Asn-Val-Ala-Glu-Asn-Ala (SEQ ID NO:1) and salts thereof; and, a physiologically acceptable carrier.

9. The formulation as in claim 8 wherein the compound has at least one biological property substantially similar to TGF-β.

* * * * *

UNITED STATES PATENT AND TRADEMARK OFFICE
CERTIFICATE OF CORRECTION

PATENT NO. : 5,661,127
DATED : August 26, 1997
INVENTOR(S) : Bhatnagar et al.     page 1 of 2

It is certified that error appears in the above-indentified patent and that said Letters Patent is hereby corrected as shown below:

On the Title Page, Section [56], under OTHER PUBLICATIONS, second reference to a publication:
    replace "Regulation of Cell Differentiation by dorsalin-1, a Novel" with:

--Regulation of Cell Differentiation by *dorsalin-1*, a Novel--

On Page 2, Section [56], under OTHER PUBLICATIONS, seventh reference to a publication:
    replace "(hOP-1) Induces New Bone Formation in Vivo with a" with:

--(hOP-1) Induces New Bone Formation *in Vivo* with a--

In Column 2, line 32:
    replace "in vivo studies have confirmed some of the more promising" with:

--*in vivo* studies have confirmed some of the more promising--

In Column 2, lines 31, 33 and in Column 5, line 29, 67:
    replace "in vitro" with:

--*in vitro*--

UNITED STATES PATENT AND TRADEMARK OFFICE
CERTIFICATE OF CORRECTION

PATENT NO. : 5,661,127
DATED : August 26, 1997
INVENTOR(S) : Bhatnagar et al.

page 2 of 2

It is certified that error appears in the above-indentified patent and that said Letters Patent is hereby corrected as shown below:

In Column 6, line 27:
replace "nonbiodegradable, and may be chemically or biologicall" with:

--nonbiodegradable, and may be chemically or biologically--

In Column 11, line 30, Claim 2:
replace "a peptide having the amino aid sequence Ala-Asn-Val-" with:

--a peptide having the amino acid sequence Ala-Asn-Val- --

Signed and Sealed this

Fifth Day of May, 1998

Attest:

Attesting Officer

BRUCE LEHMAN

Commissioner of Patents and Trademarks